United States Patent [19]

Westernacher et al.

[11] 4,373,999
[45] Feb. 15, 1983

[54] DISTILLATION OF BUTINEDIOL-1,4

[75] Inventors: Helmut Westernacher, Haltern; Karl Aertken, Dülmen, both of Fed. Rep. of Germany

[73] Assignee: GAF-Hüls Chemie GmbH, Marl, Fed. Rep. of Germany

[21] Appl. No.: 363,550

[22] Filed: Mar. 30, 1982

[30] Foreign Application Priority Data

Apr. 8, 1981 [DE] Fed. Rep. of Germany ....... 3114153

[51] Int. Cl.³ ...................... B01D 3/34; C07C 33/046
[52] U.S. Cl. .......................................... 203/6; 203/18; 203/64; 203/72; 203/73; 568/856
[58] Field of Search .................... 568/855, 856; 203/6, 203/64, 89, 38, 18, 72, 73, 71, DIG. 11

[56] References Cited

U.S. PATENT DOCUMENTS

| | | | |
|---|---|---|---|
| 2,895,886 | 7/1959 | Schneider | 203/72 |
| 3,129,252 | 4/1964 | Graham et al. | 568/856 |
| 3,154,589 | 10/1964 | Moore | 568/855 |
| 3,282,800 | 11/1966 | Lang | 203/6 |
| 3,644,179 | 2/1972 | Knoer et al. | 203/72 |
| 3,920,759 | 11/1975 | Hort | 568/855 |

FOREIGN PATENT DOCUMENTS 698019 10/1953 United Kingdom ............... 568/855

OTHER PUBLICATIONS

Werner, Berthold et al., Chemie Ingenieur Technik, vol. 47, No. 9, (1975) pp. 368-373.

Primary Examiner—Wilbur L. Bascomb, Jr.
Attorney, Agent, or Firm—Wells & Wells

[57] ABSTRACT

A process permitting hazard free purification by distillation of compounds which are distillable per se but which present the risk of explosive decomposition under the effect of elevated temperatures. A desensitizing substance is added to the compounds to be distilled.

Aliphatic alcohols for instance are suitable additives for alkinols.

Examples are provided for the distillation of butinediol-1,4 together with the additive glycerin.

5 Claims, 1 Drawing Figure

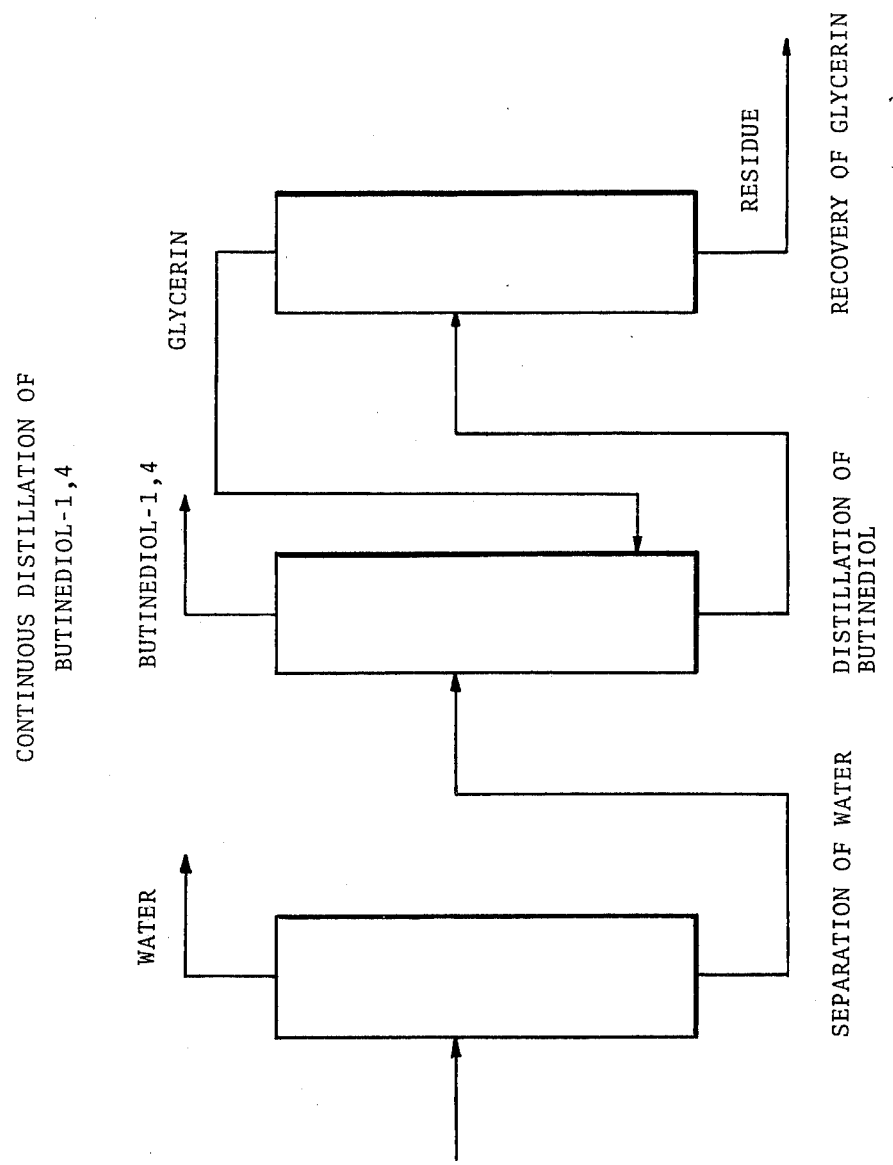

DISTILLATION OF BUTINEDIOL-1,4

CROSS-REFERENCE TO A RELATED APPLICATION

Applicants claim priority under 35 U.S.C. 119 for application No. P 31 14 153.6 filed Apr. 8, 1981 in the Patent Office of the Federal Republic of Germany.

BACKGROUND OF THE INVENTION

The field of the invention is the purification of butinediol-1,4 (2-butyne-1,4-diol) and the invention is particularly concerned with this purification by distilling butinediol-1,4 without danger.

The state of the art of purifying butinediol-1,4 by distillation may be ascertained by reference to the Kirk-Othmer, "Encyclopedia of Chemical Technology", Vol. 1 (1963), pages 602–609, particularly the section on Health and Safety Factors on page 607, the disclosures of which are incorporated herein.

It is known, for example from Kirk-Othmer, ibid., page 607, that butinediol-1,4 decomposes spontaneously beyond a temperature which depends on the purity of the product and this temperature can vary upward and downward. This decomposition can take place explosively. This foreseeable hazard of butinediol-1,4 requires special precautions during the necessary purifying operations, whereby the purification procedures frequently are costly in terms of the steps which must be applied.

Thus in practice purified butinediol-1,4 is obtained from the approximately 35% aqueous solution resulting from the production of butinediol. This 35% aqueous solution is treated with activated carbon and following filtration, the water is removed under vacuum at about 80° to 90° C. for example through the head into a falling film evaporator. The dehydrated butinediol is discharged from the sump.

As observed above, a purification of the raw product has been very risky when distillation is used.

SUMMARY OF THE INVENTION

Having in mind the limitations of the prior art it is an object of the present invention to purify butinediol-1,4 by distillation without danger where butinediol-1,4 presents a risk of explosive decomposition under the influence of temperature.

According to the present invention a process was discovered for the hazard free distillation of butinediol-1,4, which tends to spontaneous decomposition under temperature, by adding a desensitizingly effective substance to the butinediol-1,4 being distilled.

The process of the present invention permits the lowering of the safety risks of a sudden, explosive decomposition of the butinediol-1,4 during distillation by the addition of a substance acting in a desensitizing manner so that the distillation can be carried out without danger.

Surprisingly it has been discovered that a substance as common and economical as glycerin is remarkably well suited as a desensitizing substance in the distillation of butinediol-1,4.

Glycerin is suitable for continuous and discontinuous distillation.

This substance furthermore offers the advantage that it does not react with the compound to be distilled and can itself be easily separated by distillation.

Glycerin offers another advantage by being an additive already effective in relatively slight proportions and moreover permitting repeated use. For instance it can be used 20 times for distillation batches (Example 1) without intermediate purification.

The quantitative ratio (weight ratio) of the butinediol-1,4 compound to be distilled and the desensitizing glycerin additive should be between about 1:2 and 2:1 at the beginning of the distillation, preferably between 1:1 and 2:1.

For reasons of economy, the ratio of butinediol-1,4 to glycerin should not be less than 1:2. For reasons of safety a ratio of more than 2:1 should be avoided.

When observing these quantitative ratios, the decomposition temperature of butinediol-1,4 can be raised by up to 40° C. The addition of the glycerin during the distillation represents another advantage in that an incipient decomposition can run its course much more slowly, whereby danger to plant and environment can be avoided.

BRIEF DESCRIPTION OF THE DRAWING

The FIGURE of the drawing is a schematic showing of the apparatus for carrying out the evaporation of the crude butinediol followed by the distillation with glycerin of the present invention.

DESCRIPTION OF THE PREFERRED EMBODIMENT

Specific examples of distillations of butinediol-glycerin mixtures were carried out with 33.3 and 50% by weight of glycerin, and a comparison example was run with butinediol-1,4 without glycerin.

Prior to the application of the inventive concept during the distillation, the behavior of the mixture of substances was investigated in a pressurized heat-blocking reactor as disclosed by W. Berthold et al, in CHEMIE INGENIEUR TECHNIK, Vol. 47, No. 9 (1975), page 368.

The Evaporation

The starting material is generally a 35% aqueous solution of crude butinediol such as the crude butinediol produced by the U.S. Pat. No. 3,920,759. This aqueous solution is concentrated by evaporation in a falling film evaporator at temperatures of about 80° to 100° C. and a vacuum of about 460 to 1015 mbar until a $H_2O$-concentration of about 0,1 to 1 weight % is reached. The water is separated by the discontinuous procedure in the same distillation apparatus, in which also the butinediol is distilled. By the continuous run the water can be separated in any distillation apparatus, for example also in a falling film evaporator.

The Distillation

The concentrated butinediol crude from the evaporation is mixed with glycerin in a weight ratio of about one part butinediol-1,4/two parts glycerin to two parts butinediol-1,4/one part glycerin and placed in a distillation apparatus. The distillation is carried out at a sump temperature of about 150° to 200° C. and a pressure of about 1 L to 5 mbar. Pure (greater than 99% butinediol-1,4) is obtained at the top of the distillation apparatus and the glycerin remains in the sump for use with more crude butinediol.

Arrangement of the Test Apparatus 200 to 400 g of the samples used are placed within a thin-walled V4A stainless steel vessel. The vessel containing the sample is separated by two silvered glass containers and a silvered lid from the environment, namely a thermostatically controlled 2-liter V4A stainless steel autoclave, and in this manner an extensively adiabatic operation is facilitated.

The temperatures at the various sites in the system are measured by thermocouples. The pressure is recorded continuously by a strain gauge element.

Profile of the Test Method

The autoclave at the temperature of reaction and provided with the sample to be tested is placed in an aluminum block acting as the thermostat and is set at the reference temperature. At a setting of 200° C., the autoclave will reach the reference temperature after about 1 hour, and the sample, due to the thermal insulation after about 8 to 10 hours. Data concerning the exothermal reaction behavior are obtained from the recorded temperature and pressure curves.

COMPARISON EXAMPLE

At a preset temperature of 200° C., pure butinediol very rapidly turns into an explosive reaction. When glycerin is added, a substantially lesser exothermal reaction takes place, showing the desensitizing effect of the glycerin. The critical temperature threshold of a 50% by weight butinediol-glycerin mixture compared to pure butinediol is shifted upward by about 35° C.

The following specific examples illustrate the advantageous effects of the process of the present invention.

EXAMPLE I 250 g of crude butinediol-1,4 are mixed with 250 g of glycerin (ratio of 1:1) in a laboratory distillation apparatus (column cross-section: 25 mm, metal packing: about 7 to 10 theor. plates; sump content: 1 liter) and subjected to discontinuous distillation. The crude butinediol was obtained from an approximately 35% aqueous butinediol solution by evaporating the water at about 80 to 90° C. (the butinediol-1,4 content in the crude butinediol is 95% by weight). For a pressure of 2 mbars and a sump temperature of 160° to 180° C., the pure butinediol went through the head at 115° to 120° C., (purity 99% by weight). No noticeable decomposition of the butinediol was observed. The applied glycerin was used for 20 distillation batches. Thereupon it was purified by distillation, 150 g being recovered which were suitable for reuse. The remainder was discharged together with the contaminations from the crude butinediol.

EXAMPLE 2

The procedure is the same as in Example 1, but the butinediol-glycerin ratio is 2:1 at the beginning of the discontinuous distillation. The results were comparable to Example 1.

We claim:

1. In the process for purifying butinediol-1,4 by distillation, the improvement comprising:
    adding glycerin to the butinediol-1,4 to be distilled.

2. The process of claim 1, characterized in that the quantitative ratio of butinediol-1,4 to glycerin at the beginning of the distillation is between about 1:2 and 2:1.

3. The process of claim 1, characterized in that the quantitative ratio of butinediol-1,4 to glycerin at the beginning of the distillation is between 1:1 and 2:1.

4. A process for purifying butinediol-1,4 comprising:
    (a) evaporating an approximately 35% by weight aqueous solution of butinediol-1,4 at a temperature of about 80° to 90° C. and separating water and a crude butinediol containing about 95% by weight butinediol-1,4; and
    (b) carrying out a distillation of said crude butinediol mixed with glycerin in a weight ratio of about one part butinediol-1,4 to one part of said glycerin at a sump temperature of about 115° to 120° C. and a pressure of about 2 mbars and separating said butinediol-1,4 from said glycerin.

5. The process of claim 4, further comprising:
    (c) adding additional crude butinediol to step (b).

* * * * *